United States Patent [19]

Volpenhein

[11] 4,263,216
[45] Apr. 21, 1981

[54] DIGLYCERIDE MANUFACTURE

[75] Inventor: Robert A. Volpenhein, Cincinnati, Ohio

[73] Assignee: The Procter & Gamble Company, Cincinnati, Ohio

[21] Appl. No.: 953,303

[22] Filed: Oct. 20, 1978

[51] Int. Cl.$^3$ ............................................. C11C 3/02
[52] U.S. Cl. .................................................. 260/410.7
[58] Field of Search ..................................... 260/410.7

[56] References Cited

U.S. PATENT DOCUMENTS

| | | | |
|---|---|---|---|
| Re. 28,737 | 3/1976 | Yetter | 260/410.7 |
| 2,442,532 | 1/1948 | Eckey | 260/410.7 |
| 2,727,913 | 12/1955 | Kuhrt | 260/410.7 |
| 3,012,890 | 12/1961 | Dutton | 260/410.7 |
| 3,312,724 | 4/1967 | Harwood | 260/410.7 |
| 3,492,130 | 1/1970 | Harwood | 260/410.7 |
| 4,154,749 | 5/1979 | Kranack | 260/410.7 |

Primary Examiner—John F. Niebling
Attorney, Agent, or Firm—Michael J. Roth; Jerry J. Yetter; Richard C. Witte

[57] ABSTRACT

Saturated triglycerides are reacted with glycerol in the presence of either a glycerolysis catalyst or a preformed glycerate to provide a product which is a mixture of monoglycerides, triglycerides, 1,2-diglycerides and 1,3-diglycerides. The mixture is stored in the presence of a low temperature rearrangement catalyst at a storage temperature below the melting point of the glyceride ester components of the mixture and substantially all of the mixture is converted into 1,3-diglycerides. In this way there are prepared, for example, 1-palmitoyl,3-stearoyl diglyceride, 1,3-distearoyl diglyceride and 1,3-dipalmitoyl diglyceride, which are appropriate precursors for the synthesis of confectioner's hard butters, and the like.

25 Claims, No Drawings

DIGLYCERIDE MANUFACTURE

TECHNICAL FIELD

This invention encompasses a process for producing 1,3-diglycerides from triglycerides. The 1,3-diglyceride materials produced in the practice of this invention can subsequently be esterified at the middle (2) position using art-disclosed, position-specific esterification processes to provide triglyceride mixtures suitable for use as confectioner's hard butter, and the like. Accordingly, the present invention provides a means whereby the triglycerides present in naturally occurring sources such as palm oil and soybean oil can be converted to 1,3-fatty acid diglycerides, which are the basic raw materials for the manufacture of cocoa butter, and the like.

As described more fully hereinafter, the manufacture of 1,3-diglycerides has received considerable attention from workers in the field of oil and fat chemistry and several processes for manufacturing 1,3-diglycerides are known. However, the art-disclosed processes suffer from various disadvantages, including low yield of the desired 1,3-diglyceride product, the need for unacceptably long conversion times, the need to use (and remove) organic solvents, and the like.

It is well known that confectioner's butters such as cocoa butter are rather unusual among the naturally occurring fats. For example, cocoa butter is normally a brittle solid up to about 25° C., has a relatively narrow melting range and is almost completely liquid slightly above body temperature. These unique melting characteristics make cocoa butter suitable for use in confectionery products, especially chocolates. Such melting characteristics contribute glossy coatings, absence of stickiness and favorable volume changes during confectionery product molding.

Because of these advantageous melting characteristics and because of the demand for the properties which cocoa butter imparts to confectionery products, large quantities of this expensive commodity are imported even when domestic fats which can be used to produce synthetic cocoa butter are in plentiful supply at much less than the cost of cocoa butter. For many years, therefore, attempts have been made to provide from readily available and cheaper fats a product that can be used to replace at least part of the cocoa butter in chocolates and other confectionery products that normally contain cocoa butter.

In this search it has been determined that cocoa butter's advantageous physical characteristics are derived from the arrangement of the fatty acid substituents in its glycerides. Analyses have shown that cocoa butter comprises principally 1-palmitoyl-2-oleoyl-3-stearoyl glycerol, 1-palmitoyl-2-oleoyl-3-palmitoyl glycerol and 1-stearoyl-2-oleoyl-3-palmitoyl glycerol. The presence of triglycerides in cocoa butter having oleoyl groups at other than the 2-position, and correspondingly, having palmitoyl and stearoyl groups at other than the 1- and 3-positions, undesirably affects the melting properties of the butter.

From the foregoing, it will be appreciated that the manufacturing process of the present invention which can convert fatty acid triglycerides to mixtures containing primary 1,3-diglycerides having fatty acid residues in the palmitoyl-stearoyl range provides the critical 1,3-diglyceride starting material for synthesizing cocoa butter and other confectioner's butters.

BACKGROUND ART

Lutton, "Technical Lipid Structures," *J. Amer. Oil Chem. Soc.*, 49, pp. 1-9 (1972) describes the interconversion of 1,2-diglycerides to 1,3-diglycerides on storage.

U.S. Pat. No. 3,845,087, issued to Degroot (1974) also describes the isomerization of 1,2-diglycerides to 1,3-diglycerides. This isomerization is accomplished in the solid state within 20° C. of the initial melting point of the 1,2-diglyceride. This U.S. patent appears to correspond with British Pat. No. 1,369,438.

Eckey and Formo, *J. Amer. Oil Chem. Soc.*, 26, pp. 207-211 (1949) describe a method of preparing saturated diglycerides or saturated monoglycerides by directed interesterification of triglyceride mixtures containing free hydroxyl groups.

U.S. Pat. No. 2,875,066, issued to Holman and Going (1959) describes a low temperature "directed interesterification" of glycerides. The conditions are such that the desired glyceride is simultaneously crystallized from the reaction.

U.S. Pat. No. 2,558,547, issued to Eckey (1951) describes a catalytic ester-ester interchange at temperatures not substantially exceeding 120° C. The reaction was carried out using finely divided and suspended alkali metal hydride as the catalyst.

U.S. Pat. No. 3,012,890, issued to Dutton, et al. (1961) relates to a process for preparing a mixture of 1,3-diglycerides by reacting glycerin, tripalmitin, tristearin and triacetin. The random mixture of diglycerides is separated and crystallized.

U.S. Pat. No. 2,206,167, issued to Edeler and Richardson (1940) discloses the preparation of mono- or diglycerides by reacting glycerin, a triglyceride and soap at temperatures above 150° C.

U.S. Pat. No. 3,312,724, issued to Harwood (1967) describes a method for preparing symmetrical 1,3-diglycerides by reacting glycerin with triglycerides and a catalyst in the presence of a solvent.

U.S. Pat. No. 3,492,130, issued to Harwood (1970) is related to hard butter compositions. In Example I of this patent a process for preparing 1,3-dipalmitin from tripalmitin and glycerin is described.

U.S. Pat. No. 3,634,473, issued to Harwood (1972) describes a process for preparing pure symmetrical diglycerides by a glycerolysis process. "The improvement resides in first liquifying a substantially anhydrous mixture of glycerol and triglyceride fat, then adding a low temperature rearrangement catalyst to the liquified mixture and agitating the catalyst-containing liquified mixture until a symmetrical diglyceride is formed by equilibration in the liquid mixture. Crystallization of the symmetrical diglyceride is induced. . . ."

The following references teach the use of catalysts and acid halides for manufacturing 2-oleoyl triglycerides suitable for use as confectioner's butters from 1,3-diglycerides of the type prepared in the manner of this invention.

U.S. Pat. No. 3,809,711, above, discloses the perfluorinated sulfonic acids preferred for use in the esterification step of the present process.

U.S. Pat. Nos. 3,410,881 and 3,337,596 disclose the use of perchloric acid as an effective catalyst for preparing a cocoa butter substitute without rearrangement of the ester groups. However, perchloric acid is known to be explosive and its use in the presence of organic compounds in commercial scale syntheses can be dangerous.

Another known method for synthesizing a cocoa butter substitute comprises reacting a diglyceride having palmitoyl and stearoyl groups at the 1- and 3-positions with oleoyl chloride; see U.S. Pat. No. 3,012,890. Furthermore, it is known in the prior art that, in general, acid chlorides can be used to specifically esterify mono- and diglycerides. The use of acid chlorides for specific esterifications has many undesirable aspects, however. For instance, acid chlorides are very corrosive and their use involves handling problems. Besides, hydrochloric acid, a by-product of the reaction of an acid chloride with a hydroxyl group, is difficult to remove from the oleaginous reaction product, a critical factor inasmuch as the product is to be used as a food.

Feuge, Willich and Guice, the Journal of the American Oil Chemists Society, July 1963, pp. 260–64, demonstrate that ester group rearrangement ordinarily occurs during the esterification of partial glycerides, and, at page 260, point out that hydrochloric, sulfuric and hydrocarbyl sulfonic acids, which are widely used as esterification catalysts, cause ester group rearrangement. Accordingly, these acid catalysts are not suitable for preparing the desired position-specific (i.e., 2-oleoyl) triglycerides for use as a cocoa butter substitute. Similarly, ester group rearrangement ordinarily occurs during esterification of partial polyol esters other than glycerides, e.g., during esterification of partial 1,2-propylene glycol esters.

Gramstad, et al., J. Chem. Soc. 4069, 1957, teach the use of trifluoromethane sulfonic acid as an esterification catalyst but do not suggest that it would be useful in the preparation of triglycerides without ester rearrangement. Moreover, the previously noted Feuge, et al., article suggests that sulfonic acid esterification catalysts per se cause ester group rearrangement.

U.S. Pat. No. 3,882,155 discloses the use of trinitrobenzene sulfonic acid as a position-specific esterification catalyst for synthesizing cocoa butter.

U.S. Pat. No. 3,808,245 discloses boron trifluoride as a position-specific esterification catalyst for synthesizing cocoa butter.

U.S. Pat. No. 3,989,728 discloses metal halides as position-specific catalysts in synthetic cocoa butter processes.

The disclosures of all the foregoing patents and articles are incorporated herein by reference.

DISCLOSURE OF INVENTION

The present invention encompasses a process for preparing saturated 1,3-diglycerides, comprising the steps of: (a) reacting substantially saturated triglycerides (TG) with a reactant selected from glycerol (G) plus glycerolysis catalyst (C) or pre-formed glycerage (PFG), to provide a glycerolysis product which comprises a mixture of monoglycerides (MG), triglycerides (TG), 1,2-diglycerides (1,2-DG) and 1,3-diglycerides (1,3-DG); and (b) storing the glycerolysis product of Step (a) in the presence of a low temperature rearrangement catalyst (LTRC) at a storage temperature below the melting point of the glyceride components of said glycerolysis product for a storage period of at least about 4 hours.

Schematically:

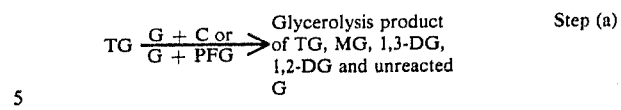

The glycerolysis product which results from Step (a) comprises glycerate esters, as follows: ca. 30% TG, ca. 25% MG, ca. 45%–50% combined, 1,3-DG and 1,2-DG. Of the DG esters produced in Step (a), ca. 65% are the desired 1,3-DG and ca. 35% are undesired 1,2-DG. It is to be understood that, in the practice of this invention, the glycerolysis product resulting from Step (a) need not be separated into its components prior to proceeding to Step (b) as follows:

The Final Product of the overall reaction comprises ca. 5% TG, ca. 5% MG and ca. 90% DG, of which ca. 95%, or greater, is in the desired 1,3-DG form, and some free fatty acid.

For preparing 1,3-diglycerides used in the manufacture of confectioner's butters, and the like, the substantially saturated triglyceride used in this process will comprise a triglyceride having carboxylic acid residues in the chain length range of from about $C_{10}$ to about $C_{20}$, especially in the range from about $C_{12}$ to about $C_{18}$. Accordingly, the process can be carried out with "hardened" (i.e., substantially saturated or hydrogenated to be substantially saturated) triglycerides derived from such sources as soybean oil, palm oil, coconut oil, sunflower oil, safflower oil, cottonseed oil, tallow and the like, and mixtures thereof, which are non-limiting examples of the triglycerides used herein.

The preferred process herein for preparing 1,3-diglycerides useful in the manufacture of confectioner's butters is carried out at a mole ratio of triglyceride to glycerol or glycerol-plus-glycerate in the range of from about 0.5:1 to about 3:1, most preferably at a ratio of about 2:1.

Hydrogenated palm oil is especially useful for preparing a 1,3-diglyceride product which can subsequently be used to manufacture confectioner's cocoa butter.

Best Mode

The two-step process of this invention comprises a glycerolysis step and a rearrangement step. When carried out under the conditions disclosed herein, the process converts saturated triglyceride mixtures to product mixtures which comprise high proportions of 1,3-diglycerides. Although various conditions and catalysts can be successfully used in the process, as disclosed more fully hereinafter, the following is preferred and is easily scaled up for commercialization.

500 grams of hardened palm oil previously heated to 120° C. was added to a one-liter flask containing 28 grams of glycerol and 2 grams of powdered sodium hydroxide. The flask was equipped with a stirrer, thermometer and vacuum take-off tube. The mixture was heated and stirred at 120° C. under vacuum (1 mm. Hg) for 30 minutes. After cooling to 70° C. the glycerolysis mix was solidified and ground in a mill under nitrogen.

A portion of the glycerolysis mix was removed and analyzed for composition by gas chromatographic carbon number profile and thin layer chromatography (TLC).

| FFA* | MG | DG | TG | Other |
|------|------|------|------|-------|
| 1.5  | 21.7 | 53.6 | 22.8 | 0.3   |

*"FFA" denotes free fatty acids.

The mixture contained about 15% 1,2-diglyceride by TLC.

The balance of the mix was divided into two portions, sealed in jars under nitrogen, and stored at 50° C. for either 24 or 48 hours. At the end of the storage time, the samples were again analyzed.

| Storage Time at 50° C. | FFA | Mono | Di | Tri | Others |
|---|---|---|---|---|---|
| 24 hours | 1.7 | 9.9 | 83.3 | 4.7 | 0.4 |
| 48 hours | 1.6 | 6.0 | 86.2 | 6.2 | 0.1 |

By TLC analysis 1,2-diglyceride amounted to less than 5% of the mix after 24 and 48 hours storage.

When the glycerolysis step of the foregoing process is carried out properly, the conversion of triglycerides to diglycerides consistently gives 85% yields of the di-products within 24 hours. The maximum rate of conversion to diglycerides can be obtained by reacting simultaneously fat, glycerol and sodium hydroxide at 120° C. under vacuum for a maximum of 30 minutes, followed by cooling and storage at 50° C. This eliminates the need for pre-making the glycerate catalyst and a second low temperature addition of fresh rearrangement catalyst, as disclosed hereinafter.

Further testing has confirmed that the glycerolysis catalyst is heat sensitive and its usefulness as a low temperature rearrangement catalyst can be destroyed during glycerolysis at 120° C. Therefore, to eliminate the need for fresh catalyst after glycerolysis the temperature/time cycle used for glycerolysis must be held to a minimum. The conditions recommended above are designed to operate within these parameters.

| Glycerolysis Time | % Diglyceride After 24 Hrs. Storage at 50° C. |
|---|---|
| 30 min. | 82 |
| 60 min. | 78 |
| 120 min. | 54 |

In an alternate mode, the glycerolysis step can be carried out at higher temperatures or for longer periods of time. However, it is to be understood that the glycerolysis catalyst can be wholly or partly inactivated/decomposed under such conditions. If the glycerolysis catalyst is deactivated, additional catalyst must be added to effect the rearrangement reaction of Step (b).

The reaction mechanism hypothesized for the present process is as follows.

Step (a) The glycerolysis step of the present process is a base-catalyzed random interesterification. The added base catalyst reacts with glycerol or partial glycerides to form a glycerate anion or a mono- or diacyl glycerate anion. For example:

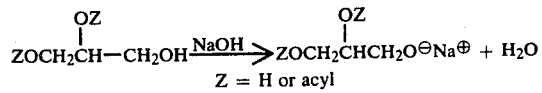

Z = H or acyl

Thus, the added base "catalyst" does not remain unchanged in the reaction medium. Rather it is a reactant which forms the true catalyst (glycerate anions) in situ. Accordingly, the term "catalyst" as applied to the added bases, such as NaOH or NaOCH$_3$, in Step (a) means catalysts in the sense that they cause the formation of glycerate anion, as described here.

The resulting glycerate anion reacts with other glyceride molecules by attacking the carbonyl carbon of the fatty acid chains, i.e.:

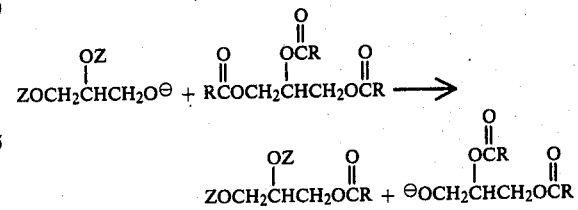

This process of exchange of acyl groups continues until an equilibrium distribution of mono-, di-, and triglycerides is attained. This equilibrium distribution is determined by the relative amounts of fatty acid chains and hydroxyl groups in the reaction mixture. Formo, J. Am. Oil Chem. Soc. 31, 548 (1954) has calculated this distribution as a function of the ratio of glycerol to fat assuming random esterification of the available hydroxyl groups; at lower levels of glycerol (less than ca. 2 moles per mole of fat) where most of it is soluble in the fat, these calculated values agree fairly well with observed values.

Step (b) In the rearrangement step of this process the composition of the mixture from Step (a) is shifted strongly towards 1,3-diglyceride. This is accomplished by maintaining the mixtures containing catalyst at a temperature below the melting point of the glycerides in the mixture. Possibly, the 1,3-diglyceride crystallizes and is then no longer a part of the equilibrating system, while other glyceride components continue to undergo ester interchange reactions. The physical form of these other glycerides is not known; however, the reacting mixture is a hard solid with little or no apparent liquid phase. Another possible explanation of this directing effect is that in the solid state the 1,3-diglyceride is significantly more thermodynamically stable than the other glycerides (monoglyceride, triglyceride, 1,2-diglyceride) due to the crystal structures of the various species; if differences in thermodynamic stability are sufficiently large, then the observed directing to the 1,3-diglyceride could occur even if all of the glyceride species (including the 1,3-diglyceride) remain a part of the equilibrating system.

In Step (a) the amount of catalyst used is 2 mole percent to 10 mole percent of the triglyceride, preferably 4 to 8 mole percent.

The amount of rearrangement catalyst to be added to the reaction mixture from Step (a) will vary, depending on the conditions under which glycerolysis has been carried out. As disclosed, under mild glycerolysis conditions, catalyst carry-out suffices to effect Step (b). Alternatively, up to about 4 mole percent base rearrangement catalyst (calculated on total moles of diglyceride) is added to the reaction mixture of Step (a) to effect Step (b).

Industrial Applicability

The present process can be carried out using various art-disclosed materials.

Glycerolysis Step (a) is carried out at a temperature above about 75° C., more preferably from about 100° C. to about 200° C., most preferably about 100° C. to about 120° C. At temperatures from above about 120° C., the glycerolysis catalyst may be inactivated and unavailable for Step (b). If inactivation occurs, fresh rearrangement catalyst is added subsequent to Step (a) to effect the rearrangement of Step (b).

Glycerolysis catalysts useful herein include the alkali metal soaps (at glycerolysis temperatures above about 150° C.), the alkali metal alkoxides (e.g., sodium methoxide, sodium ethoxide, potassium isopropoxide, and the like), alkali metal hydrides (e.g., NaH) and the alkali metal hydroxides (i.e., LiOH, NaOH, KOH, RbOH and CsOH). The pre-formed alkali metal glycerates can also be used.

Sodium hydroxide is the most preferred, least expensive glycerolysis catalyst for use in Step (a) of the present process.

Rearrangement Step (b) is carried out by storing the reaction product produced in glycerolysis Step (a) at a temperature below the melting point of the glyceride components of said reaction product. That is, the reaction product is stored at a temperature of about 60° C., or below, whereupon it solidifies. Storage is preferably carried out below about 55° C., more preferably at a temperature in the range from about 20° C. to about 50° C., most preferably about 50° C.

The storage temperature used in the rearrangement Step (b) is especially critical, in that temperatures above about 55° C. reduce the yield of 1,3-diglyceride, and yields obtained at storage temperatures above about 60°–65° C. are generally unacceptable in commercial practice.

Rearrangement catalysts used in Step (b) include the alkali metal alkoxides and alkali metal hydroxides as disclosed for use hereinabove as the glycerolysis catalyst. The alkali metal soap glycerolysis catalysts useful in Step (a) are not useful as the rearrangement catalyst in Step (b) since they effect ester interchange reactions only at high temperatures and do not produce the desired high yields of 1,3-diglycerides.

Preferably, the rearrangement catalyst used in Step (b) is selected from sodium methoxide, sodium ethoxide, and is most preferably sodium hydroxide.

The storage period of Step (b) is at least about 4 hours, more preferably about 12 hours, most preferably from about 24 hours to about 48 hours. Periods less than about 4 hours result in mixtures containing about 60% diglyceride; at 24 hours under the present conditions the 1,3-diglyceride yield approaches 85%, or greater. Storage times longer than 48 hours do not increase yields to any great extent.

The present process can be used to provide a mixture of 1,3-distearoyl diglyceride, 1,3-dipalmitoyl diglyceride and 1-palmitoyl, 3-stearoyl diglyceride, which is especially useful in the manufacture of confectioner's butters whose properties closely mimic those of natural cocoa butter. One such process comprises reacting hydrogenated palm oil with a reactant selected from glycerol plus glycerolysis catalyst or pre-formed glycerate, at a mole ratio of hydrogenated palm oil to glycerol (or glycerol-plus-glycerate) of about 2:1, said reaction being carried out at a temperature above about 75° C., to provide a glycerolysis product which is a mixture comprising predominantly glycerol and monoglycerides, triglycerides, 1,2-diglycerides and 1,3-diglycerides having stearoyl and palmitoyl fatty acid residues; and storing the aforesaid glycerolysis product in the presence of a rearrangement catalyst at a storage temperature of about 50° C. for a storage period of at least about 10 hours, whereupon a product comprising greater than about 80% by weight of said desired 1,3-diglycerides is secured.

The aforesaid process for preparing precursors for cocoa butter, or the like, preferably employs a storage period from about 24 hours to about 48 hours in Step (b). Preferably, the process uses NaOH as the glycerolysis catalyst in Step (a). The rearrangement catalyst of Step (b) is selected from sodium hydroxide (preferred), sodium methoxide or sodium ethoxide. As an additional step, the rearrangement catalyst is neutralized with acid as disclosed hereinafter, following Step (b).

Commercially available, substantially unsaturated natural fats and oils can be hardened (hydrogenated) and used in the aforesaid process for preparing 1,3-diglycerides especially adapted for use in the manufacture of confectioner's butter, or the like. One such process comprises mixing hardened soybean oil and hardened palm oil in a ratio sufficient to provide a mole ratio of stearic acid residues:palmitic acid residues in the range of from about 1:1 to about 2.5:1; reacting said mixture with a reactant selected from glycerol plus glycerolysis catalyst or pre-formed glycerate, to provide a glycerolysis product which comprises a mixture of glycerol, monoglycerides, triglycerides, 1,2-diglycerides and 1,3-diglycerides; and storing the glycerolysis product in the presence of a rearrangement catalyst at a storage temperature below the melting point of said glycerolysis product for a storage period of at least about 4 hours.

As before, when using natural, unsaturated fats or oils, the glycerolysis catalyst is preferably sodium hydroxide and the rearrangement catalyst is preferably selected from sodium hydroxide, sodium methoxide or sodium ethoxide. The most highly preferred process is wherein the glycerolysis catalyst is sodium hydroxide; the rearrangement catalyst is sodium hydroxide; and wherein the rearrangement is carried out at a temperature of about 50° C. for a period of from about 24 hours to about 48 hours. Again, as an additional step, the rearrangement catalyst is preferably neutralized following rearrangement.

The following Examples illustrate the practice of this invention but are not intended to be limiting thereof.

EXAMPLE I

Preparation of 200 Pounds of Diglyceride 180 pounds of hardened palm oil and 20 pounds of hardened soybean oil stock were mixed, vacuum dried in a Pfaudler reactor and cooled to 80° C. To this mix was added 11.5 pounds of sodium glycerate in glycerol previously prepared by reacting 9.3 wt.% NaOH pellets (9.3% by weight of glycerol) with glycerol under vacuum (1 mm. Hg) at 120° C. The reaction mix was stirred and heated to 120° C., held for 30 minutes and the reactor cooled to 80° C. Vacuum was broken with argon. 0.4 pounds sodium methoxide powder was added, with stirring for 10 minutes.

The mix was drained into 50 pound cans and these were sealed under nitrogen and stored at 50° C. for 7 days, and then held at room temperature for one week. The resulting product was predominantly diglyceride and was labeled "Distock."

The product was ground through a Model D-O-1 Clawson Mfg. Co. "Snowdrift." Two passes through the machine yielded six 50 pound cans of coarsely ground Distock.

About 25 pounds of the foregoing Distock were ground to a fairly fine powder. This was then neutralized as follows:

75 pounds hexane, 18 pounds H₂O containing 0.5 pounds of acetic acid and 8 pounds methyl alcohol were combined. Distock (25 pounds) was added and stirred for 30 minutes. The mixture was heated to 55° C. and stirred at this temperature for 15 minutes. The layers were allowed to separate and the water layer was decanted off. 18 pounds H₂O were added, heated to 55° C. with stirring for 15 minutes and allowed to separate. The hexane solution was placed in large trays to let the hexane evaporate. The solution was allowed to evaporate over a 2-day period; the product was placed in an air oven for 2 days, and then ground in mill to a fine powder.

The product recovered from the foregoing process and neutralization comprised greater than 85% diglycerides; of the diglycerides, greater than 95% were the desired 1,3-diglycerides, as shown.

| FFA | MG | DG* | TG | Other |
|---|---|---|---|---|
| 4.4 | 5.4 | 86.8 | 1.8 | 1.7 |
| Normalized | 5.7 | 92.3 | 1.9 | |

*Total 1,2- and 1,3-diglycerides.

The product prepared in the foregoing manner was of food grade quality suitable for use in the manufacture of confectioner's butter, or the like.

EXAMPLE II

One gram mole of the 1,3-diglyceride product of Example I is heated with one gram mole of oleoyl chloride in a glass reaction vessel until HCl evolution ceases. The resulting product is neutralized with aqueous NaOH and dissolved in hexane. After decolorization (activated carbon) the hexane is evaporated. The resulting product is suitable for use as a confectioner's butter to manufacture chocolate candy bars, and the like.

EXAMPLE III

Hydrogenated palm oil (acid value 0; iodine value 8) is treated in the manner disclosed under the Best Mode section, hereinabove, to provide a 1,3-diglyceride product (ca. 90% purity). The 1,3-diglyceride is allowed to react with oleic anhydride in the presence of trifluoromethane sulfonic acid in the manner described in U.S. Pat. No. 3,809,711, the disclosures of which are incorporated herein by reference.

Thus, 60 grams of the 1,3-diglyceride mixture prepared in the foregoing manner are admixed with 250 grams of a 1:1 mixture of oleic acid and oleic anhydride. One ml. of trifluoromethane sulfonic acid is added to the mixture and the reactants are stirred together at room temperature for one hour. An equal volume of water is added to the reaction mixture, which is then heated to 70° C.-100° C. for one hour to hydrolyze excess oleic anhydride. The water is removed by draining and the residue is extracted five times with equal volumes of methanol to remove traces of free acid. The residue is substantially pure triglyceride product.

The synthetic triglyceride product prepared in the manner of Example III is compared with commercially-available, natural cocoa butter as follows. Samples of the synthetic triglyceride and of commercially-available cocoa butter are melted; chilled in ice for five minutes; are held for one day at ca. 21° C.; are held for one week at ca. 26° C.; and are held overnight at ca. 10° C. The solids content at these various temperatures are determined at the end of the period by the dilatometric method as described in Fulton, Lutton and Willie, Journal of the American Oil Chemists Society, March 1954, vol. XXXI, No. 3, pp. 98–103. Comparison of the "melting" curves for the synthetic triglyceride product and for the commercially-available cocoa butter shows that the synthetic product has similar consistencies to natural cocoa butter over the range of temperatures from about 26° C. to about 35° C., i.e., that range of temperatures over which cocoa butter has its unique melting characteristics.

In the procedure of Example III, the trifluoromethanesulfonic acid is replaced by an equivalent amount of trifluoromethanesulfonic anhydride, pentafluoroethanesulfonic anhydride, perfluoroisopropylsulfonic acid, heptafluoropropanesulfonic acid, perfluorooctadecanesulfonic acid, perfluorocyclohexanesulfonic acid, perfluorotricosanesulfonic acid, perfluoro(decane-1,10-disulfonic) acid, hydrobromic acid, and perchloric acid, respectively, and equivalent results are secured in that a synthetic cocoa butter is secured from the 1,3-diglyceride starting material made in the manner of this invention.

EXAMPLE IV

The preparation of synthetic cocoa butter using the reaction processes of Example III is modified, as follows. The hardened palm oil starting material is replaced by an equivalent amount of mixtures of hardened palm oil and hardened soybean oil to yield various 1,3-diglycerides having molar ratios of stearic acid residues to palmitic acid residues over the range from 1:1 to about 2.5:1. After the trifluoromethanesulfonic acid-catalyzed reaction with oleic anhydride, a range of confectioner's butters with a spectrum of desirable melting properties are secured.

What is claimed is:

1. A process for preparing saturated 1,3-diglycerides without need for organic solvent extraction of undesired glycerides, comprising the steps of:
   (a) reacting substantially saturated triglycerides with a reactant selected from glycerol plus glycerolysis catalyst or pre-formed glycerate to provide a glycerolysis product which comprises a mixture of monoglycerides, triglycerides, 1,2-diglycerides and 1,3-diglycerides; and
   (b) storing the glycerolysis product of Step (a) in the presence of a low temperature rearrangement catalyst at a storage temperature below the melting point of the glyceride components of said glycerolysis product for a storage period of at least about 4 hours.

2. A process according to claim 1 wherein the substantially saturated triglyceride comprises a triglyceride having carboxylic acid residues in the chain length range of from about $C_{10}$ to about $C_{20}$.

3. A process according to claim 2 wherein the chain length of the carboxylic acid residues is is the range from about $C_{12}$ to about $C_{18}$.

4. A process according to claim 2 or claim 3 wherein the substantially saturated triglyceride is derived from soybean oil, palm oil, coconut oil, sunflower oil, safflower oil, cottonseed oil or tallow, or mixtures thereof.

5. A process according to claim 4 wherein the substantially saturated triglyceride is hydrogenated palm oil.

6. A process according to claim 1 which is carried out at a mole ratio of triglyceride to glycerol or glycerol-plus-glycerate in the range of from about 0.5:1 to about 3:1.

7. A process according to claim 6 wherein the mole ratio of triglyceride to glycerol or glycerol-plus-glycerate is about 2:1.

8. A process according to claim 1 wherein the glycerolysis catalyst of Step (a) is an alkali metal hydroxide.

9. A process according to claim 8 wherein the alkali metal hydroxide is sodium hydroxide.

10. A process according to claim 1 wherein the rearrangement catalyst used in Step (b) is an alkali metal alkoxide or alkali metal hydroxide.

11. A process according to claim 10 wherein the rearrangement catalyst is selected from sodium hydroxide, sodium methoxide and sodium ethoxide.

12. A process according to claim 1 or claim 11 wherein the storage period of Step (b) is from about 24 to about 48 hours.

13. A process according to claim 1 wherein the storage temperature of Step (b) is from about 20° C. to about 50° C.

14. A process according to claim 1 for preparing a mixture of 1,3-distearoyl diglyceride, 1,3-dipalmitoyl diglyceride and 1-palmitoyl,3-stearoyl diglyceride, comprising the steps of:

(a) reacting hydrogenated palm oil with a reactant selected from glycerol plus glycerolysis catalyst or pre-formed glycerate, at a mole ratio of hydrogenated palm oil to glyercol or glycerol-plus-glycerate of about 2:1, said reaction being carried out at a temperature above about 75° C., to provide a glycerolysis product which is a mixture of predominantly glycerol and stearoyl and palmitoyl monoglycerides, triglycerides, 1,2-diglycerides and 1,3-diglycerides; and (b) storing the glycerolysis product of Step (a) in the presence of a rearrangement catalyst at a storage temperature of about 50° C. for a storage period of at least about 10 hours, whereupon a product comprising greater than about 80% by weight of said desired 1,3-diglycerides is secured.

15. A process according to claim 14 wherein the storage period of Step (b) is from about 24 hours to about 48 hours.

16. A process according to claim 1 wherein the glycerolysis catalyst of Step (a) is sodium hydroxide.

17. A process according to claim 12 wherein the rearrangement catalyst of Step (b) is selected from sodium hydroxide, sodium methoxide or sodium ethoxide.

18. A process according to claim 14 which comprises, as an additional step, neutralizing the rearrangement catalyst following Step (b).

19. A process for preparing 1,3-diglycerides especially adapted for use in the manufacture of confectioner's butter, or the like, without need for organic solvent extraction of undesired glycerides comprising preparing a mixture of hardened soybean oil and hardened palm oil in a ratio sufficient to provide a mole ratio of stearic acid residues:palmitic acid residues in the range of from about 1:1 to about 2.5:1; and (a) reacting said mixture with a reactant selected from glycerol plus glycerolysis catalyst or glycerate, to provide a glycerolysis product which comprises a mixture of glycerol, monoglycerides, triglycerides, 1,2-diglycerides and 1,3-diglycerides; and (b) storing the glycerolysis product of Step (a) in the presence of a rearrangement catalyst at a storage temperature below the melting point of said glycerolysis product for a storage period of at least about 4 hours.

20. A process according to claim 19 wherein the glycerolysis catalyst of Step (a) is sodium hydroxide.

21. A process according to claim 20 wherein the rearrangement catalyst of Step (b) is selected from sodium hydroxide, sodium methoxide or sodium ethoxide.

22. A process according to claim 20 wherein the glycerolysis catalyst is sodium hydroxide, the rearrangement catalyst is sodium hydroxide, and wherein Step (b) is carried out at a temperature of about 50° C. for a period of from about 24 hours to about 48 hours.

23. A process according to claim 19 or claim 22 which comprises, as an additional step, neutralizing the rearrangement catalyst, following Step (b).

24. A process for preparing synthetic cocoa butter, or the like, comprising esterifying the 1,3-diglyceride product of claim 14 or 19 at the 2-position with oleic acid, oleic anhydride, or mixtures thereof, in the presence of a position-specific esterification catalyst.

25. A process according to claim 24 wherein the position-specific catalyst is trifluoromethanesulfonic acid.

* * * * *